(12) United States Patent
Jenkins et al.

(10) Patent No.: US 9,999,433 B2
(45) Date of Patent: Jun. 19, 2018

(54) APPARATUS AND METHOD TO SECURE TURBINATE TO NASAL SEPTUM

(71) Applicant: Acclarent, Inc., Menlo Park, CA (US)

(72) Inventors: Thomas R. Jenkins, Alameda, CA (US); Randy J. Kesten, Mountain View, CA (US); Jessica M. Liberatore, San Mateo, CA (US)

(73) Assignee: Acclarent, Inc., Irvine, CA (US)

( * ) Notice: Subject to any disclaimer, the term of this patent is extended or adjusted under 35 U.S.C. 154(b) by 231 days.

(21) Appl. No.: 14/837,323

(22) Filed: Aug. 27, 2015

(65) Prior Publication Data

US 2017/0056036 A1    Mar. 2, 2017

(51) Int. Cl.
| | |
|---|---|
| *A61B 17/12* | (2006.01) |
| *A61B 17/24* | (2006.01) |
| *A61B 17/04* | (2006.01) |
| *A61B 17/06* | (2006.01) |
| *A61B 1/233* | (2006.01) |
| *A61M 25/10* | (2013.01) |
| *A61B 1/00* | (2006.01) |

(52) U.S. Cl.
CPC .......... *A61B 17/24* (2013.01); *A61B 1/00183* (2013.01); *A61B 1/00195* (2013.01); *A61B 1/233* (2013.01); *A61B 17/0401* (2013.01); *A61B 17/0469* (2013.01); *A61B 17/06166* (2013.01); *A61M 25/10* (2013.01); *A61B 2017/047* (2013.01); *A61B 2017/0417* (2013.01); *A61B 2017/0464* (2013.01); *A61B 2017/0475* (2013.01); *A61B 2017/06176* (2013.01); *A61B 2017/246* (2013.01)

(58) Field of Classification Search
CPC ....... A61B 17/06; A61B 17/24; A61B 17/062; A61B 17/04; A61B 17/06166; A61B 2017/0417; A61B 2017/06052; A61B 2017/06176; A61B 17/12; A61B 17/0401; A61B 17/0625
See application file for complete search history.

(56) References Cited

U.S. PATENT DOCUMENTS

| | | | |
|---|---|---|---|
| 7,026,437 B2 | 4/2006 | Shalaby et al. | |
| 7,070,858 B2 | 7/2006 | Shalaby et al. | |
| 8,070,032 B2 * | 12/2011 | Tagge | A61B 17/00234 128/898 |
| 8,979,875 B2 | 3/2015 | Gonzales et al. | |
| 2002/0161168 A1 | 10/2002 | Shalaby et al. | |
| 2010/0030031 A1 | 2/2010 | Goldfarb et al. | |
| 2011/0004057 A1 | 1/2011 | Goldfarb et al. | |
| 2012/0078118 A1 | 3/2012 | Jenkins et al. | |

OTHER PUBLICATIONS

U.S. Appl. No. 61/725,523, filed Nov. 13, 2012.

* cited by examiner

*Primary Examiner* — Victor Nguyen
(74) *Attorney, Agent, or Firm* — Frost Brown Todd LLC

(57) ABSTRACT

A method of securing a turbinate to a nasal septum includes positioning an instrument in a nostril. The turbinate and nasal septum are pierced. The instrument is used to urge a barbed suture through the pierced turbinate and nasal septum. The turbinate is medialized against the nasal septum by urging the turbinate against the septum. The barbed suture holds the turbinate in a medialized state against the nasal septum.

20 Claims, 18 Drawing Sheets

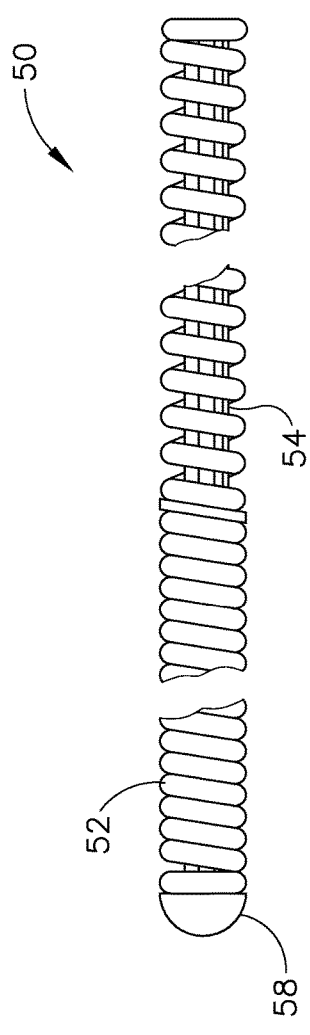
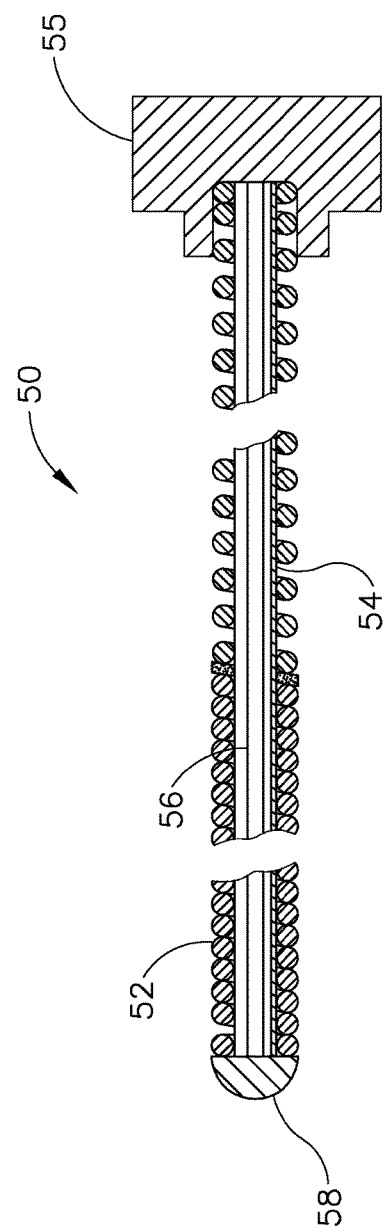

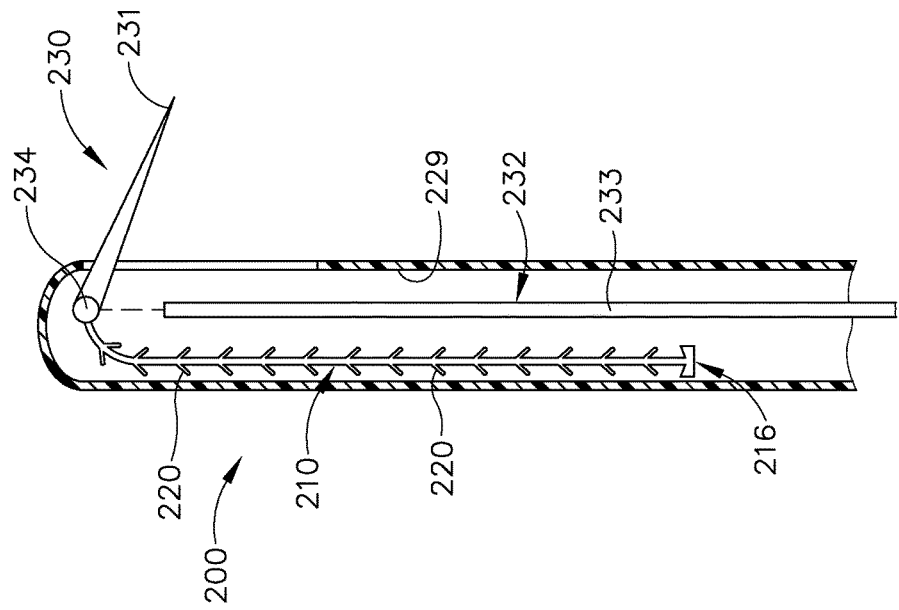
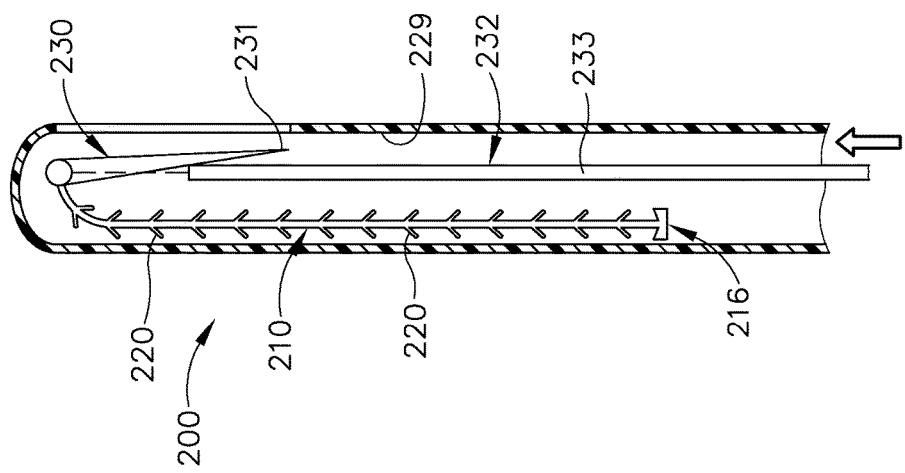

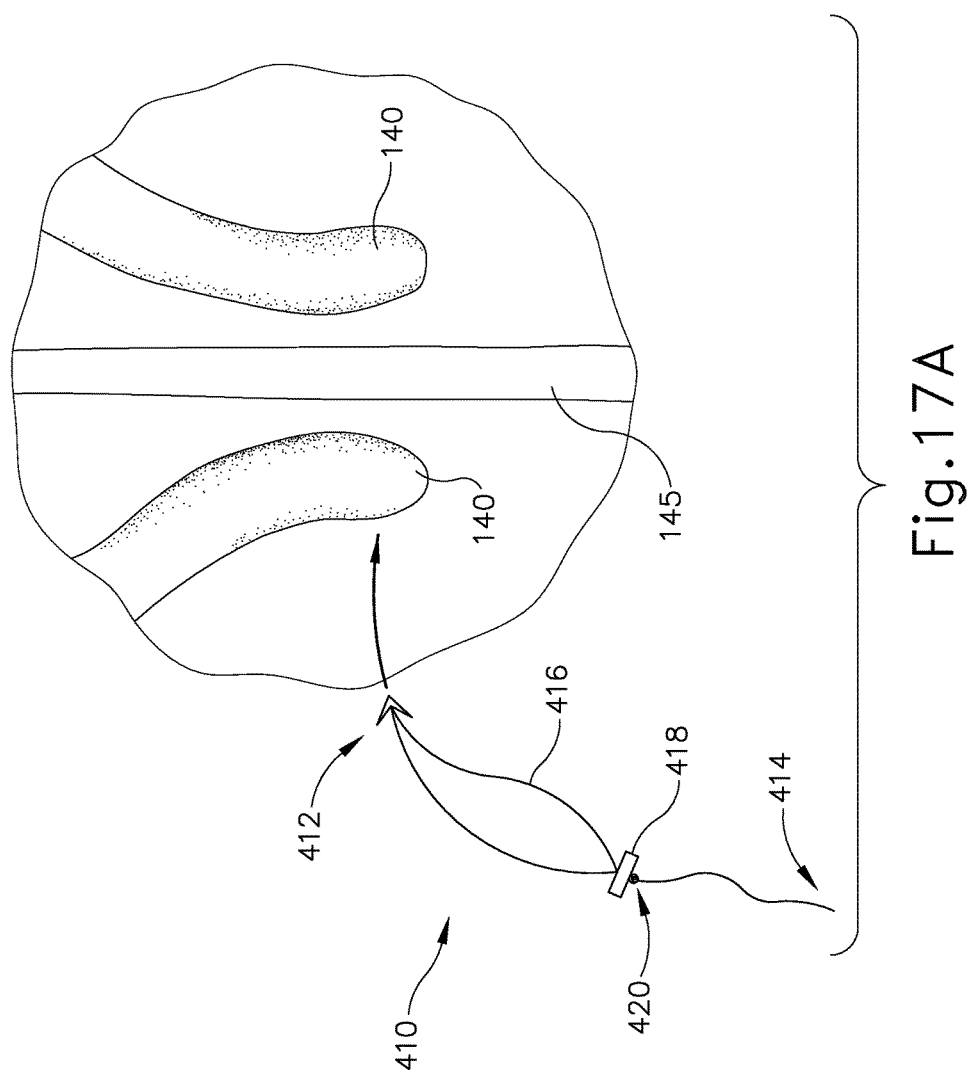

APPARATUS AND METHOD TO SECURE TURBINATE TO NASAL SEPTUM

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

While several instruments and procedures have been made and used for treatment of anatomical passageways in a patient, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a side elevational view of an exemplary illuminating guidewire suitable for use with the dilation catheter system of FIG. 1.

FIG. 3 depicts a side cross-sectional view of the illuminating guidewire of FIG. 2.

FIG. 11A depicts a side view, in partial cross-section, of an exemplary instrument for securing a turbinate to a nasal septum, showing a needle of the instrument in a stored position and the suture of FIG. 9.

FIG. 11B depicts a side view, in partial cross section, of the instrument of FIG. 11A, showing the needle of the instrument in a ready position.

FIG. 13B depicts a perspective schematic view of the suture of FIG. 9 being directed through the middle turbinate and the nasal septum to secure the middle turbinate and the nasal septum.

FIG. 17A depicts an anterior coronal cross-sectional view of a portion of a head of a patient, showing the suture of FIG. 15 after being inserted into the nasal cavity of the patient.

Figure 1:
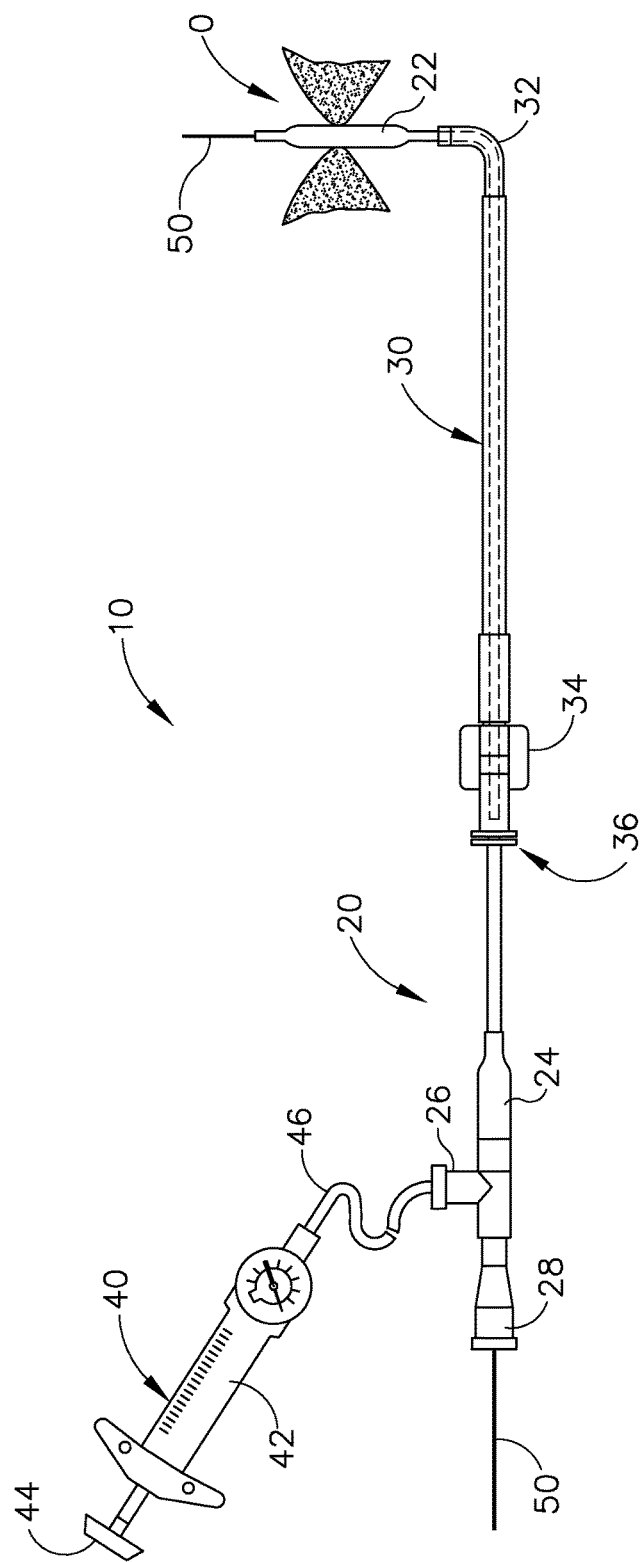
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. In some versions, inflator (40) is configured in accordance with at least some of the teachings of U.S. Pat. App. No. 61/725,523, entitled "Inflator for Dilation of Anatomical Passageway," filed Nov. 13, 2012, the disclosure of which is incorporated by reference herein. Other suitable forms that inflator (40) may take will be apparent to those of ordinary skill in the art in view of the teachings herein.

As best seen in FIGS. 2-3, guidewire (50) of the present example comprises a coil (52) positioned about a core wire (54). An illumination wire (56) extends along the interior of core wire (54) and terminates in an atraumatic lens (58). A connector (55) at the proximal end of guidewire (50) enables optical coupling between illumination wire (56) and a light source (not shown). Illumination wire (56) may comprise one or more optical fibers. Lens (58) is configured to project light when illumination wire (56) is illuminated by the light source, such that illumination wire (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, issued Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination wire (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

II. Overview of Exemplary Endoscope

Figure 4:
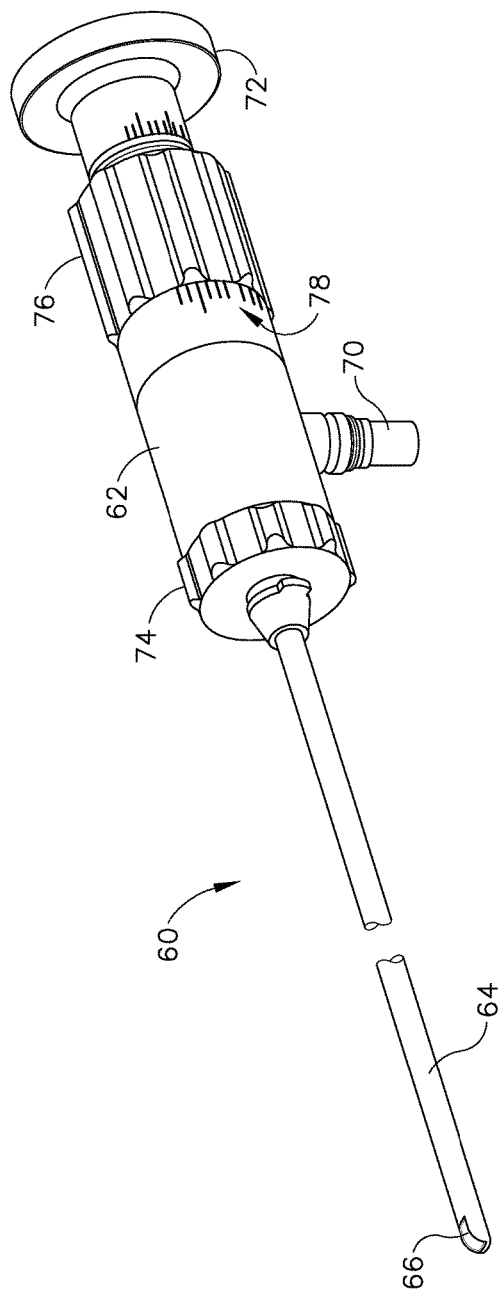
FIG. 4 depicts a perspective view of an exemplary endoscope suitable for use with the dilation catheter system of FIG. 1.
Figure 5:
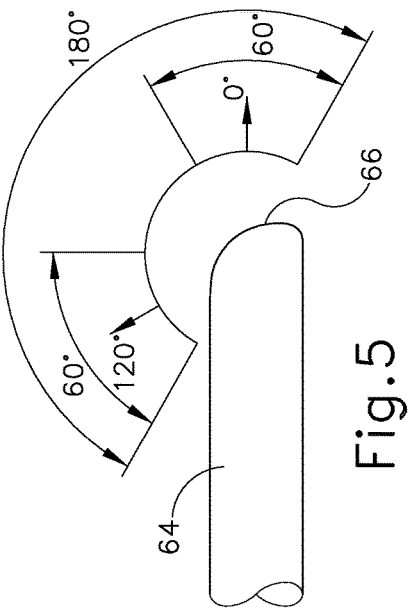
FIG. 5 depicts a side elevational view of the distal end of the endoscope of FIG. 5, showing an exemplary range of viewing angles.

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. Exemplary Apparatus for Securing Turbinate to Nasal Septum

A turbinate (or nasal conchae) is a long, narrow and curled bone shelf which protrudes into the nasal passages. Turbinates divide the nasal airway into three groove-like air passages (i.e., nasi meatae) and are responsible for forcing inhaled air to flow in a steady, regular pattern around the largest possible surface of cilia, and climate controlling tissue of the nasal passage. Turbinates are composed of pseudo-stratified columnar ciliated respiratory epithelium with a thick, vascular and erectile glandular tissue layer. The turbinates are located laterally in the nasal cavities, curling medially and downwardly into the nasal airway. There are three pairs of turbinates—superior turbinates, middle turbinates and inferior turbinates. Each pair is composed of one turbinate in either side of the nasal cavity, divided by the septum.

Aside from being responsible for nasal airflow and required for functional respiration, turbinates are also responsible for filtration, heating, and humidification of air inhaled through the nose. As air passes over the turbinate tissues it is heated to body temperature, humidified, and filtered. The respiratory epithelium of the turbinates plays a major role in the body's immunological defense. The respiratory epithelium of the turbinates is partially composed of goblet cells which secret mucus over the nasal cavities and which filters out foreign particles larger than 2 to 3 micrometers. The respiratory epithelium of the turbinates is also involved in the lymphatic system which protects the body from being infected by viruses and/or bacteria.

Figure 6:
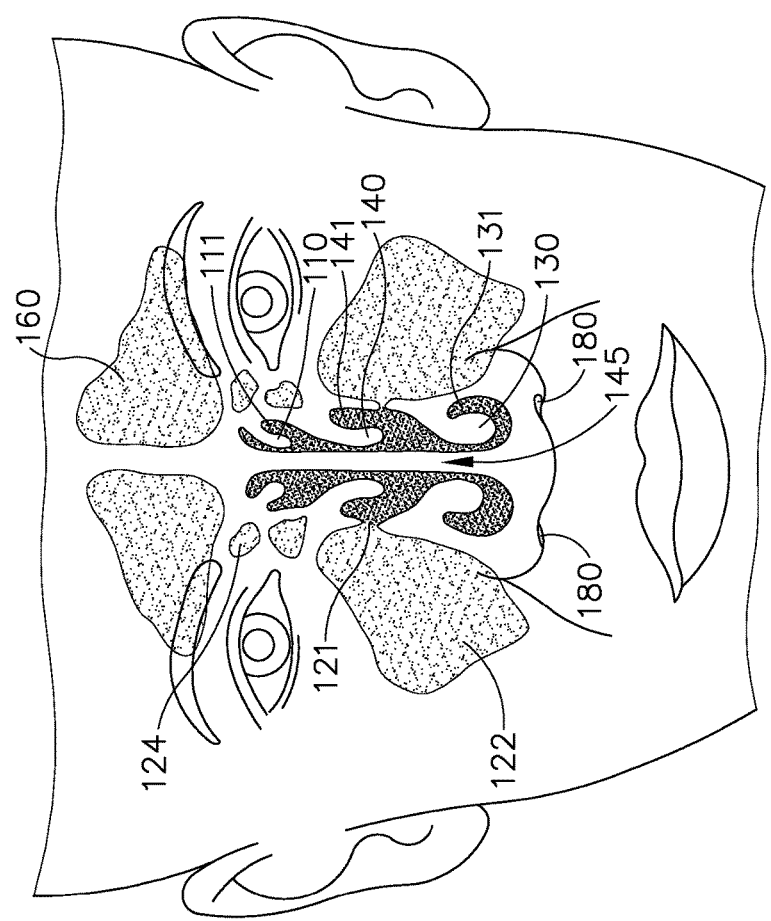
FIG. 6 depicts a front view of a human head, with a cross-section taken to show nasal turbinate structures and paranasal sinus structures.
Figure 7:
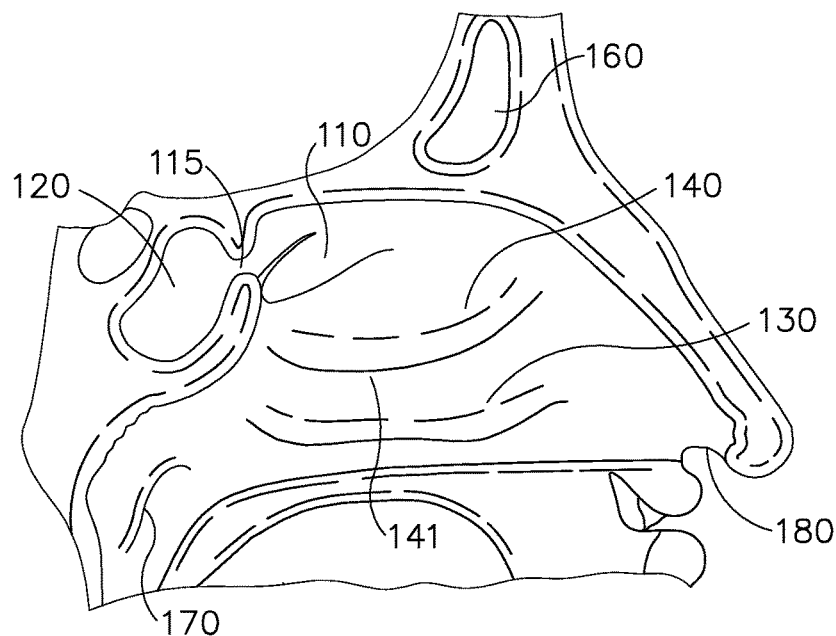
FIG. 7 depicts a sagittal cross-sectional view of a human head, showing paranasal sinus structures.
Figure 8:
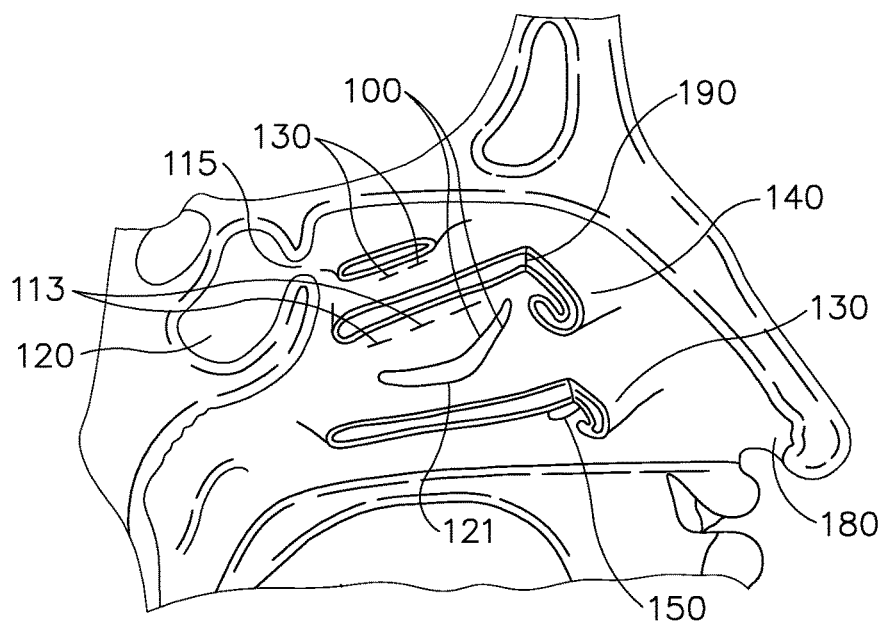
FIG. 8 depicts a modified sagittal cross-sectional view of a human head, showing paranasal structures.

Referring specifically to FIGS. 6-8, a patient's paranasal passageway includes superior turbinate (110) (near the ostium (115) of the sphenoid sinus (120)), an inferior turbinate (130), a middle turbinate (140). The nasal passageway includes a superior meatus (111), middle meatus (141), and inferior meatus (131), each of which is an air passage positioned behind a respective superior turbinate (110), middle turbinate (140), and inferior turbinate (130). The paranasal passageway communicates with the Eustachian tube via Eustachian tube opening (170).

The ostium (not shown) of the frontal sinus (160) is obstructed by the middle turbinate (140). Inferior turbinates (130) are the largest turbinates, being about three inches in length in some patients, and are responsible for the majority of airflow direction, humidification, heating, and filtering of air inhaled through the nose. Middle turbinates (140) are typically smaller than the inferior turbinates (130). In some patients, middle turbinates (140) are about two inches in length. Middle turbinates (140) project downwards over the openings of the maxillary sinus (122) and ethmoid sinuses (124), and act as buffers to protect the sinuses from coming in direct contact with pressurized nasal airflow. Most inhaled airflow travels between inferior turbinate (130) and middle turbinate (140). Superior turbinates (110) are smaller structures in most patients, connected to the middle turbinates (140) by nerve-endings, and serve to protect the olfactory bulb.

FIG. 8 shows the view of a patient's paranasal passageway of FIG. 7, but with portions of the turbinates (110, 130, 140) shown in cross-section to more clearly illustrate the location of sinus ostia and other nasal ostia with respect to the nasal turbinates (110, 130, 140). As shown, middle turbinate (140) obscures the frontal sinus ostia (90) as well as openings (100) to the anterior ethmoid cells, openings (111) to the middle ethmoid cells, and the ostium (121) of maxillary sinus (122). Thus, middle turbinate (140) is in a position that presents a risk for damaging middle turbinate (140) when access to such openings is needed during surgery, for example. Moreover, in some instances, middle turbinate (140) may block such openings more than desired, reducing air flow throughout the nasal cavity and paranasal sinuses.

During nasal surgery, as described above, surgical devices may be inserted through the nasal opening or nostril (180) of the nose to perform surgical operations, including, but not limited to, functional endoscopic sinus surgery (FESS), sinuplasty (described above), and septoplasty. In addition or in the alternative to preventing damage to structures such as the turbinates (110, 130, 140) during procedures, in some patients, one or more of the turbinates (110, 130, 140) may obstruct other anatomy, such as the nasi meatae (111, 131, 141), sinuses, or sinus ostia described above, and prevent a person from breathing effectively. Moreover, one or more of the turbinates may obstruct access to other paranasal structures for a surgical procedure. Therefore, in some instances, medializing one or more turbinates (110, 130, 140), before or after a procedure, may allow for more efficacious surgical procedures and for better air flow through the nasal anatomy. However, the below teachings are not limited to medialization of turbinates. For instance, the below teachings may be readily applied to the closing of a mucoperichondrial or mucoperiosteal flap (e.g., following septoplasty).

A. Exemplary Barbed Suture

Figure 9:
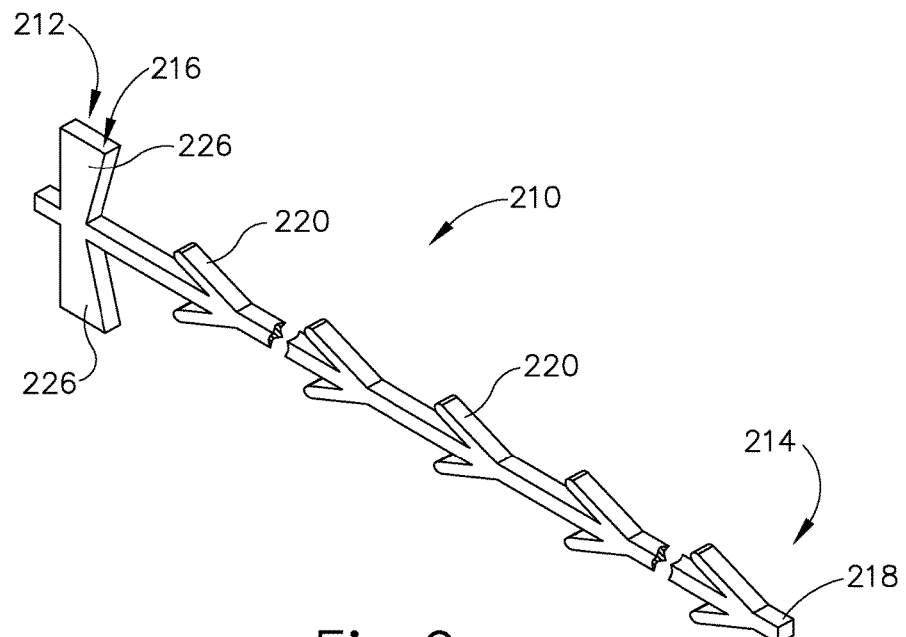
FIG. 9 depicts a perspective view of an exemplary suture.
Figure 10:
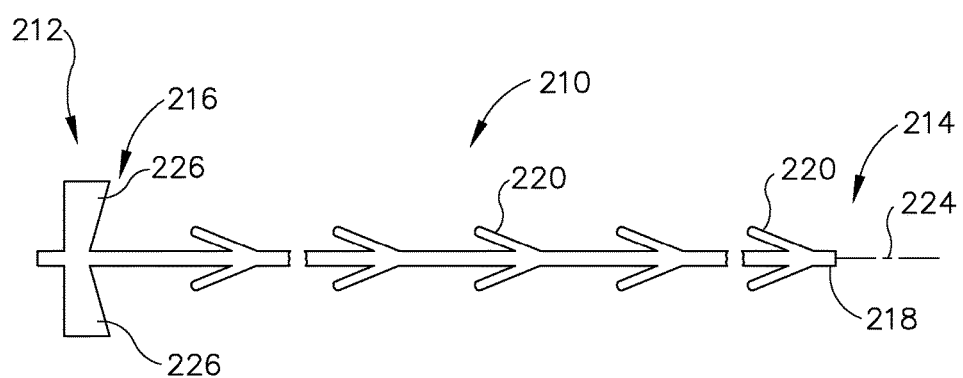
FIG. 10 depicts a side elevational view of the suture of FIG. 9.

FIGS. 9-10 show an exemplary suture (210) configured to secure one or more of turbinates (110, 130, 140) to the nasal septum (145). As shown, suture (210) includes a proximal end (212) and a distal end (214). Proximal end (212) includes an anchor (216) and distal end (214) includes a tip (218) configured to pierce and travel through tissue. Anchor (216) includes opposing arms (226) which include a proximal portion extending at an acute angle relative to axis (224). Suture (210) includes a plurality of barbs (220) longitudinally spaced along the length of suture (210). As shown, barbs (220) extend outwardly from suture body (222) away from a longitudinal axis (224) of suture (210), and towards proximal end (212). In the present example, once anchored into tissue, as discussed in further detail below, barbs (220) are configured to resist movement of suture (210) in a proximal direction. As discussed in further detail below, anchor (216) and barbs (220) together prevent the movement of suture (210) in both directions relative to tissue once barbs (220) are positioned to anchor tissue, and once anchor (216) has bottomed out against a structure, such as turbinate tissue. Suitable other configurations of anchor (216) and barbs (220) will be apparent to persons skilled in the art in view of the teachings herein.

Figure 12A:
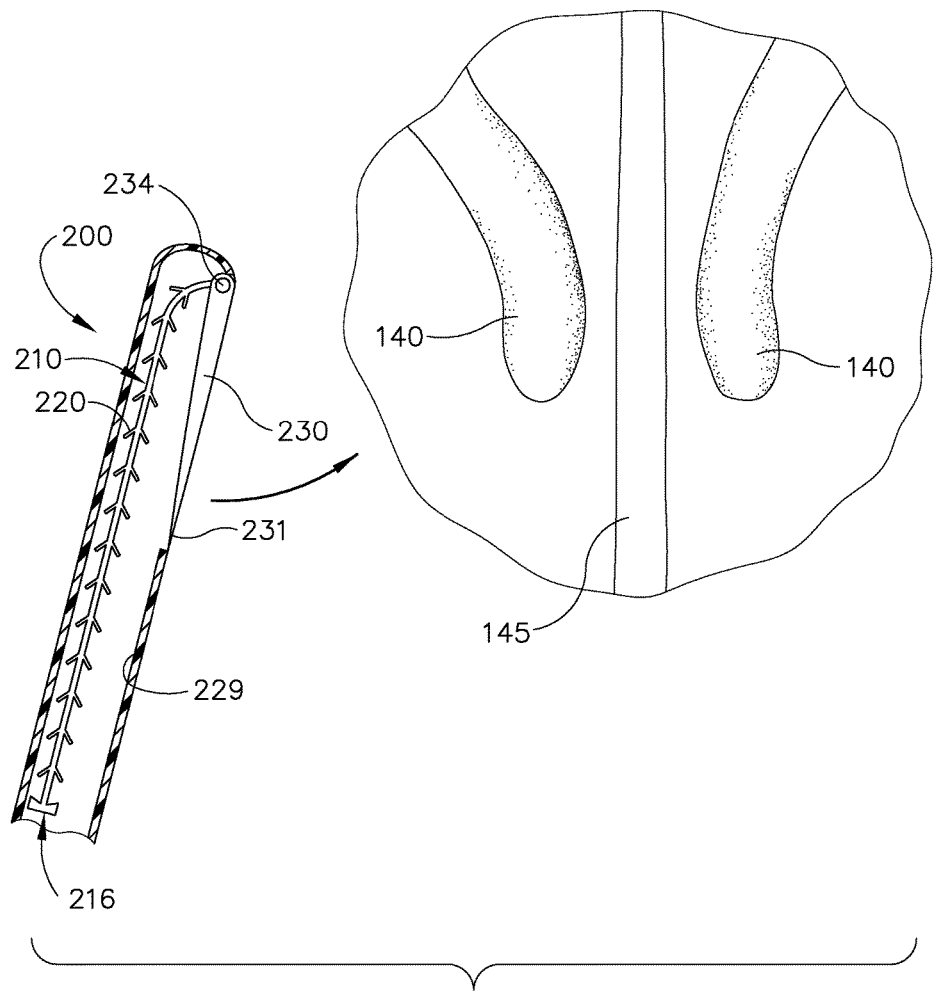
FIG. 12A depicts an anterior coronal cross-sectional view of a portion of a head of a patient, showing the instrument of FIG. 11A after being inserted into the nasal cavity of the patient, showing the needle of the instrument in a stored position.
Figure 12B:
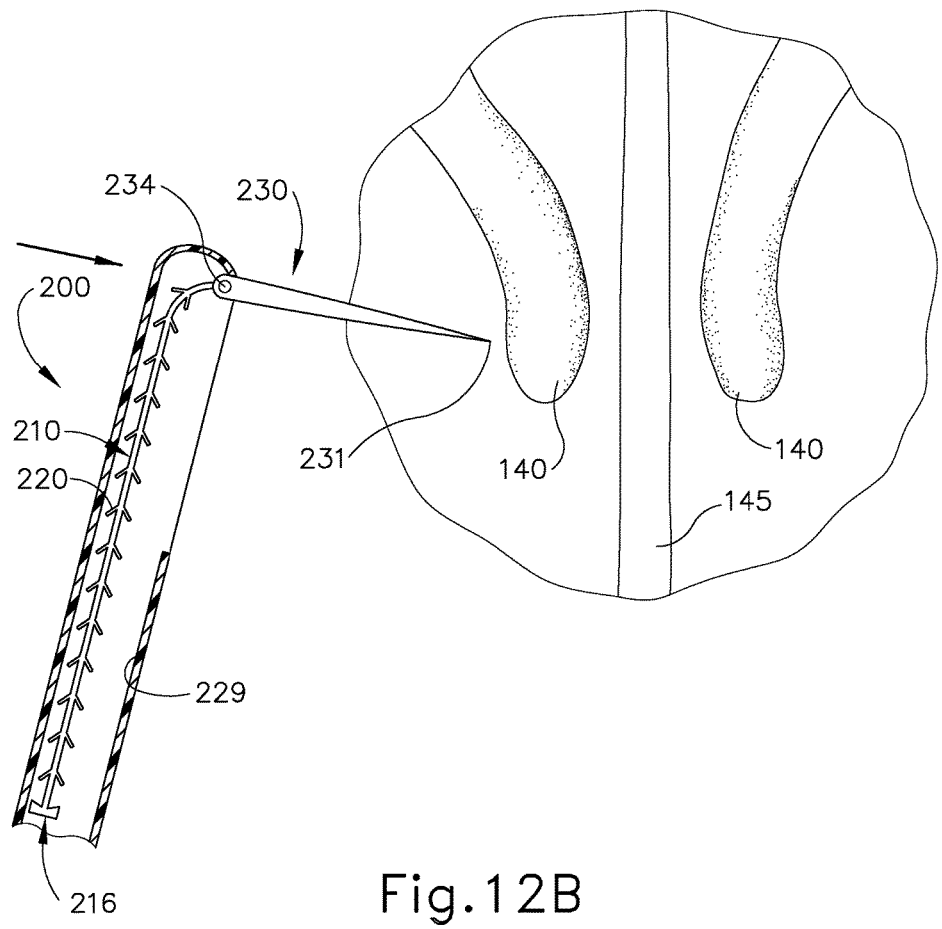
FIG. 12B depicts an anterior cross-sectional view of the portion of the head of the patient of FIG. 12A, showing the instrument of FIG. 11A after being inserted into the nasal cavity of the patient, showing the needle of the instrument in the ready position.
Figure 12C:
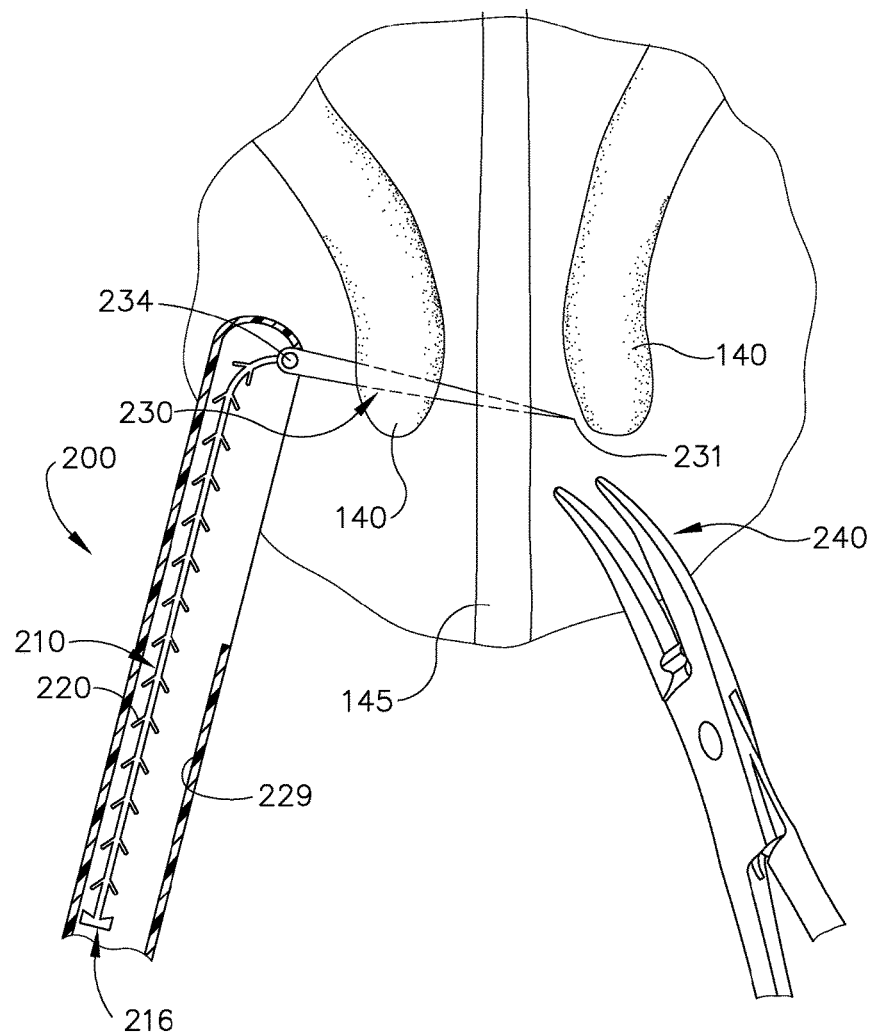
FIG. 12C depicts an anterior cross-sectional view of the portion of the head of the patient of FIG. 12A, showing the instrument of FIG. 11A after being inserted into the nasal cavity of the patient, showing the needle of the instrument in a ready position and having been directed into a middle turbinate and nasal septum.
Figure 12D:
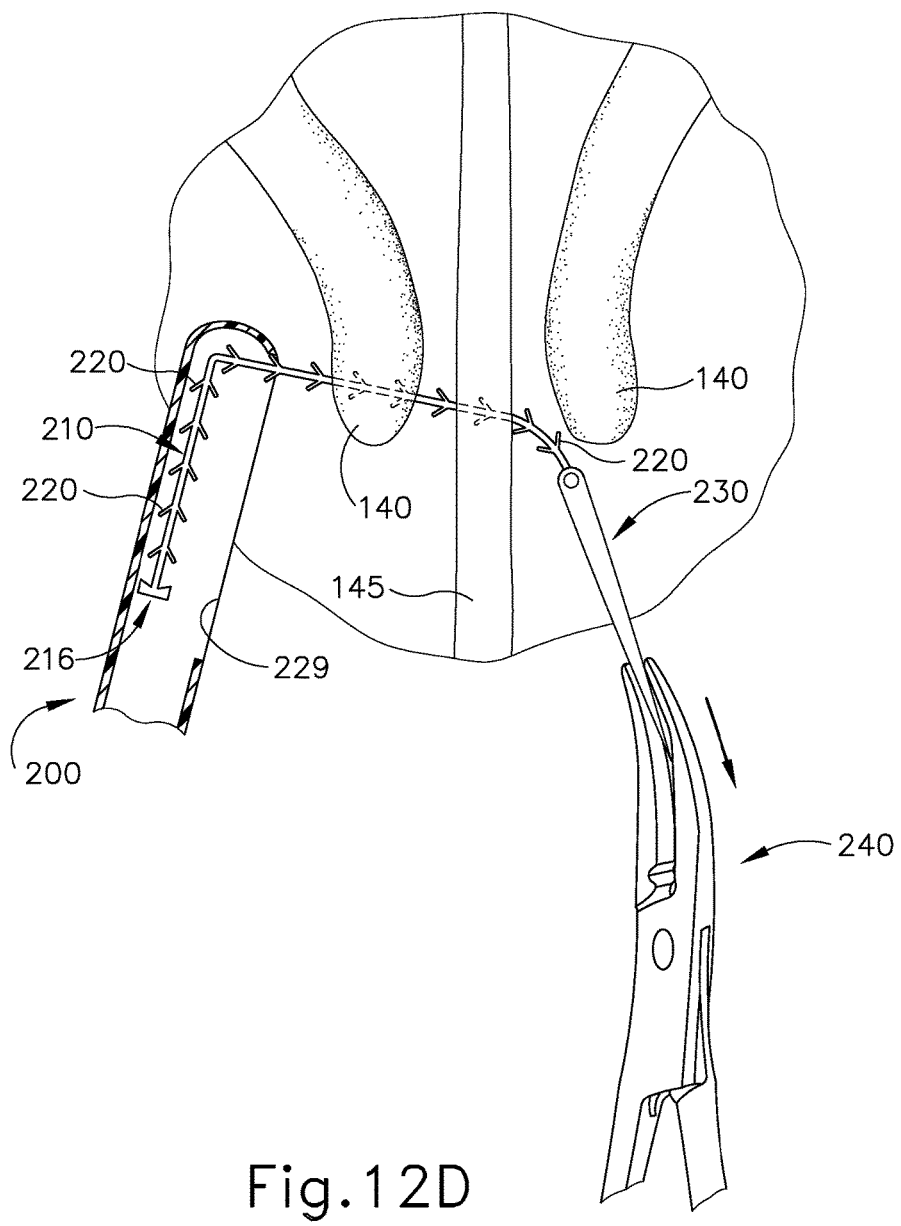
FIG. 12D depicts an anterior cross-sectional view of the portion of the head of the patient of FIG. 12A, showing the instrument of FIG. 11A after being inserted into the nasal cavity of the patient, showing the needle of the instrument being grasped by a grasping tool and the suture of the instrument being pulled from the instrument.

FIGS. 11A-12D show suture (210) incorporated into an exemplary suture delivery instrument (200). Of course, in other examples, other exemplary sutures may be incorporated into instrument (200); and suture (210) may alternatively be incorporated into other kinds of delivery instruments. Moreover, suture (210) may be provided and utilized with a conventional instrument such as conventional forceps, a conventional suturing instrument, etc. In the present example, instrument (200) is sized for insertion into a nostril and the nasal passages of a patient. As shown, instrument (200) includes a shaft (228) defining a lumen (229) which houses suture (210), needle (230), and needle actuation mechanism (232). In the present example, needle actuation mechanism (232) comprises a push rod (233). Needle (230) is operatively coupled to push rod (233) such that pushing rod (233) in the direction of arrow shown in FIG. 11A results in the needle pivoting about pivot point (234) from a stored position (FIGS. 11A, 12A) to a ready position (FIGS. 11B, 12B, 12C). Push rod (233) may be in communication with any suitable user interface feature, such as, for example, a button, a slider, a pivoting trigger, etc. In other examples, however, instead of pushing rod (233) to cause the pivoting of needle (230), a user may pull rod (233) to effectuate pivoting of needle (230). Further, instead of a push/pull rod, needle (230) may be actuated to the ready position by a push button or other actuation mechanism. Suitable other configurations for actuating needle (230) will be apparent to persons skilled in the art in view of the teachings herein. As seen in FIG. 12D and as will be further discussed below, needle (230) and suture (210) are removably coupled to shaft (228) such that needle (230) and suture (210) may be decoupled from shaft (228) when needle (230) is directed away from shaft (228).

As discussed above, in some examples, some or all of the components of instrument suture (210) may be omitted, excepted for suture (210). In some such examples, needle (230) and needle actuation mechanism (232) may be omitted. In these examples, another actuation mechanism may be provided to cause a distal end portion of the suture (210) to exit from lumen (229), which then can be directed towards one of the turbinates (110, 130, 140). In some such examples, needle (230) may be omitted. In such an example without needle (230), actuating an actuation mechanism causes a portion of suture (210) to extend from the distal end of shaft (228) at an angle toward one of the turbinates (110, 130, 140) and/or the septum (145). In such an example, a user may simply grasp suture (210), push suture (210) through turbinate (140), release the suture (210), and repeat until the suture (210) has been advanced a sufficient amount through turbinate (140) and septum (145) until the turbinate is sufficiently medialized against septum (145). In such versions, suture (210) has enough flexibility such that suture (210) may be bent to orient the tip to a position that is transverse (e.g., perpendicular) to the lateral surface of a turbinate (110, 130, 140), yet the suture (210) has enough column strength to be pushed through cartilage and adjacent tissue of at least one turbinate (110, 130, 140) and septum (145). It should also be understood that suture (210) may have an integral distal segment that is rigid and sharp (e.g., similar to a needle), thereby enabling suture (210) to be pushed through cartilage and adjacent tissue of at least one turbinate (110, 130, 140) and septum (145).

FIGS. 12A-13D show an exemplary method for securing a turbinate, such as turbinates (110, 130, 140) to nasal septum (145). While the present example shows one of the middle turbinates (140) being secured to septum (145), it will be understood that both of the middle turbinates (140) may be secured to the septum (145) using the methods described herein. Furthermore, it will be understood that such exemplary methods may be utilized to secure one or more of the superior turbinates (110) and/or one or more of the inferior turbinates (130) to the septum (145). Moreover, it will be further understood that either or both nostrils (80) may be utilized. FIGS. 12A-12B and 13A show the middle turbinate (140) spaced laterally away from the septum (145).

Figure 12E:
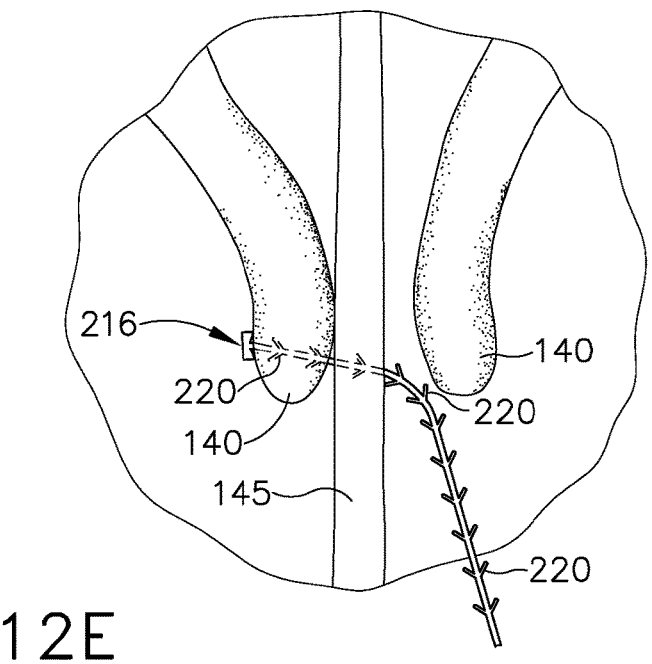
FIG. 12E depicts an anterior cross-sectional view of the portion of the head of the patient of FIG. 12A, showing the suture of FIG. 9 securing the middle turbinate and the nasal septum.
Figure 13A:
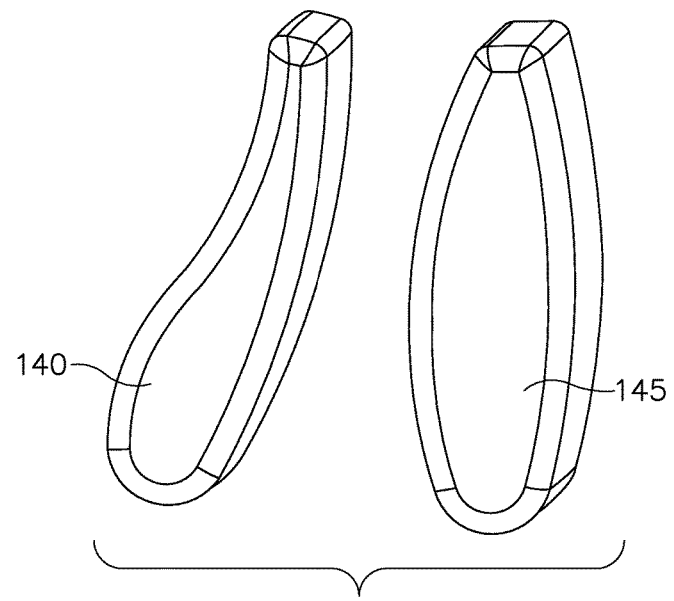
FIG. 13A depicts a perspective schematic view of a middle turbinate and a nasal septum.
Figure 13A:
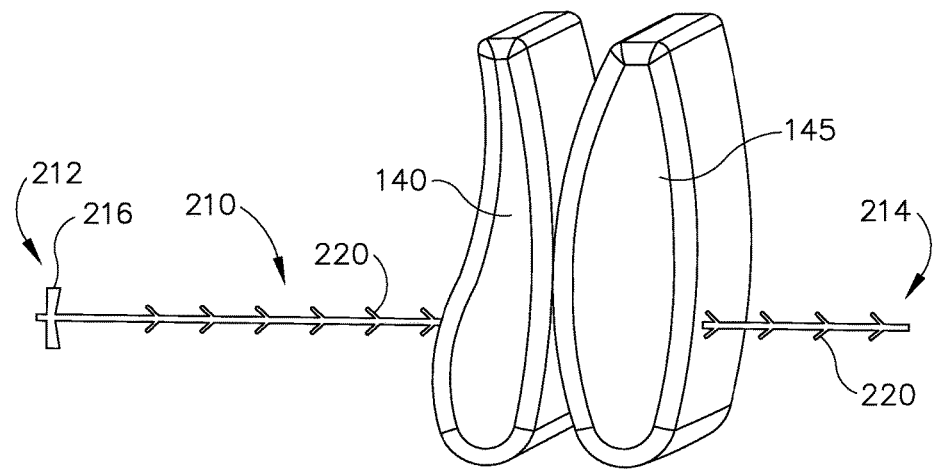
Figure 13C:
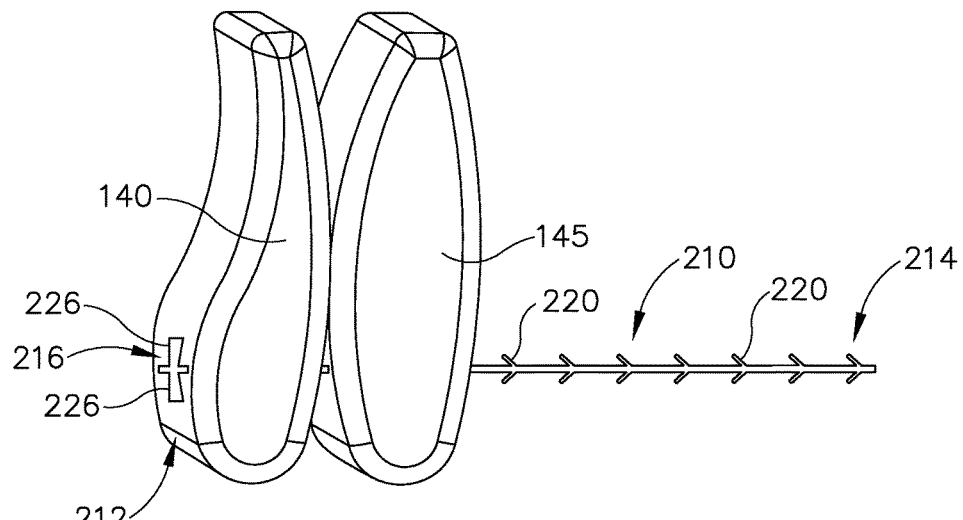
FIG. 13C depicts another perspective schematic view of the suture of FIG. 9 being directed through the middle turbinate and the nasal septum, showing an anchor of the suture abutting the middle turbinate.

As shown in FIG. 12A, a user directs instrument (200) into the nasal cavity via nostril (180) such that a distal end of instrument (200) is positioned adjacent to middle turbinate (140) on the lateral side of turbinate (140). Then, as shown in FIG. 12B, the user actuates actuation mechanism (232) in the manner discussed in detail above, in order to cause needle (230) to pivot to the ready position (FIG. 12B). Next, as shown in FIG. 12C, the user directs instrument (200) medially with needle tip (231) facing middle turbinate (140) and septum (145), and pierces middle turbinate (140) and septum (145) with needle (230) until at least a portion of needle (230) extends to the contralateral side of septum (145). As shown in FIGS. 12C-12D, the user directs a grasping tool (240) into the other nostril (80) of the patient and grasps needle (230). The user then pulls the needle (230) away from the septum (145) (e.g., toward a nostril (180)) such that suture (210) enters and is directed through middle turbinate (140) and septum (145), as shown in FIG. 13B. Eventually, anchor (216) engages middle turbinate (140). As the user continues pulling suture (210) with anchor (216) engaging middle turbinate (140), anchor (216) urges middle turbinate (140) medially into engagement with septum (145) as shown in FIGS. 12E and 13C.

Figure 12F:
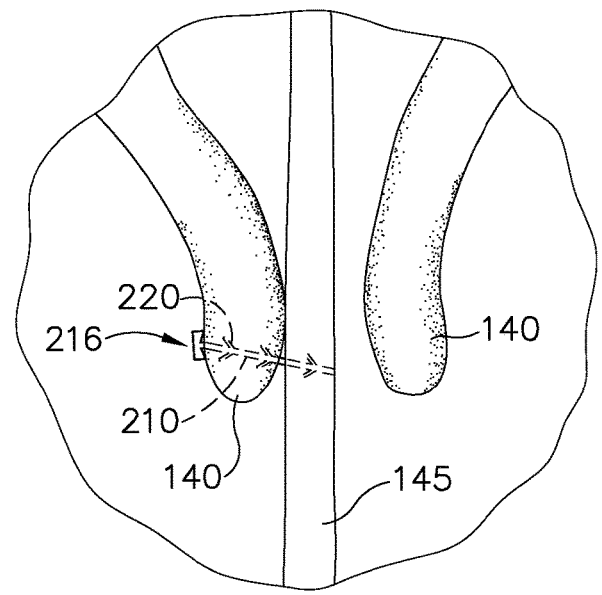
FIG. 12F depicts an anterior cross-sectional view of the portion of the head of the patient of FIG. 12A, showing the suture of FIG. 9 securing the middle turbinate and the nasal septum after a portion of the suture has been severed.
Figure 13D:
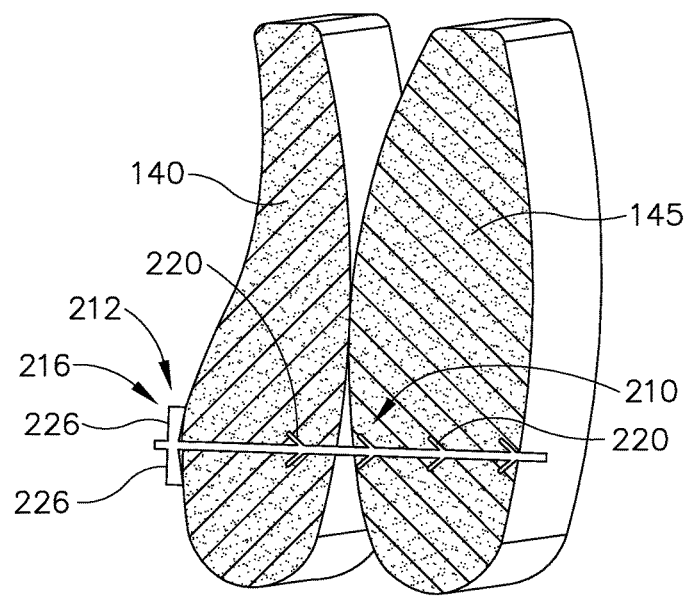
FIG. 13D depicts a schematic cross-sectional view of the suture of FIG. 9 being directed through the middle turbinate and the nasal septum, after a portion of the suture has been severed.

At this stage, barbs (220) engage portions of both the middle turbinate (140) and septum (145) such that barbs (220) prevent suture (210) from being pulled laterally out through middle turbinate (140) and septum (145). Anchor (216) prevents suture (210) from being pulled medially through middle turbinate (140). Thus, anchor (216) and barbs (220) cooperate with each other and with the tissue of middle turbinate (140) and septum (145) to maintain tension in suture (210), thereby holding middle turbinate (140) in medialized apposition with septum (145). The user may rely on tactile feedback and/or visualization (e.g., using endoscope (60), etc.) to confirm that middle turbinate (140) has been sufficiently medialized. At this stage, the user may sever the excess length of suture (210) extending laterally from the contralateral side of the septum (145), leaving the severed end of suture (210) flush with the surface of septum (145) as shown in FIGS. 12F and 13D.

Figure 14:
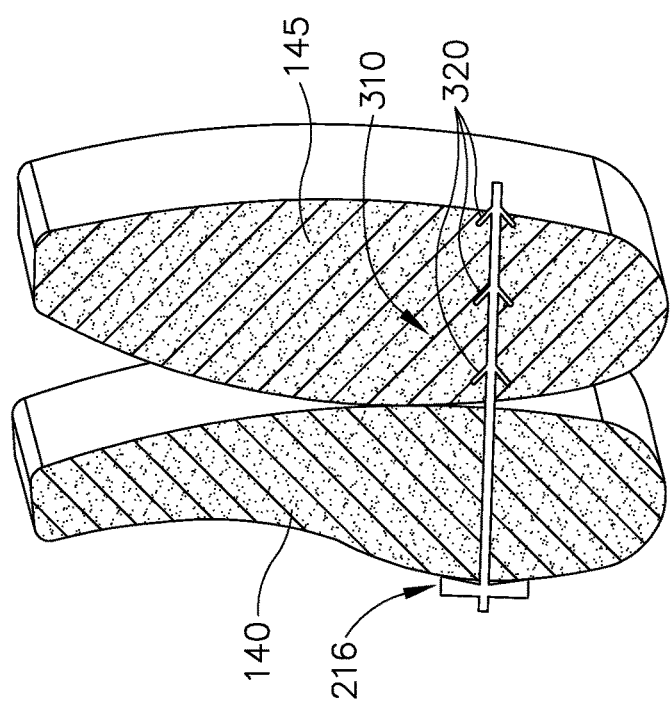
FIG. 14 depicts a schematic cross-sectional view of an exemplary alternative suture having been directed through the middle turbinate and the nasal septum, with a leading portion of the suture having been severed.

Referring to FIG. 14, in some examples, an exemplary alternative suture (310), which is suitable for incorporation into an instrument such as instrument (200), may be utilized to secure middle turbinate (140) to septum (145). In this example, suture (310) is substantially similar to suture (210), except for that barbs (320) are positioned at a spacing relative to anchor (316) that enable barbs to engage only septum (320) (i.e., barbs (320) are not positioned to engage middle turbinate (140), in most patients). Thus, in the example shown in FIG. 13, anchor (316) engages middle turbinate (140) while barbs (320) engage septum (145) in a similar manner as described above with respect to barbs (220). While the present example shows one of the middle turbinates (140) being secured to septum (145), it will be understood that both of the middle turbinates (140) may be secured to the septum (145) using the methods described herein. Furthermore, it will be understood that such exemplary methods may be utilized to secure one or more of the superior turbinates (110) and/or one or more of the inferior turbinates (130) to the septum (145). Moreover, it will be further understood that either or both nostrils (80) may be utilized.

B. Exemplary Suture with Slip Knot and Anchor

FIGS. 15 and 17A-C show an exemplary alternative suture (410) which is configured to secure one or more of turbinates (110, 130, 140) to nasal septum (145). Suture (410) is suitable for introduction into a delivery instrument, such as instrument (200) described herein. While the present example shows both of the middle turbinates (140) being secured to the septum (145), it will be understood that only one of the middle turbinates (140) may be secured to the septum (145) using the methods described herein. Furthermore, it will be understood that such exemplary methods may be utilized to secure one or more of the superior turbinates (110) and/or one or more of the inferior turbinates (140) to the septum (145). Moreover, it will be further understood that either or both nostrils (180) may be utilized.

As shown, suture (410) includes a barb (412) and a free end (414). In the example shown, suture (410) includes only a single barb (412), but it will be understood that other examples of suture (410) may include more than one barb (412). Barb (420) allows suture (410) to pass through tissue in a distal direction but is configured to resist movement of suture (410) in a proximal direction. Suture (410) further includes a loop portion (416) and an anchor member (418). Suture (410) further includes a slip knot (420) located proximally adjacent to anchor member (418). Slip knot (420) is configured such that when free end (414) is drawn away from anchor member (418), and when barb (412) is fixed in tissue, anchor (418) is drawn toward barb (412). Slip knot (420) is configured such that it resists movement of anchor (418) away from barb (412) and permits movement of anchor (418) toward barb (412). Other suitable configurations of suture (410) will be apparent to persons skilled in the art in view of the teachings herein.

Figure 16:
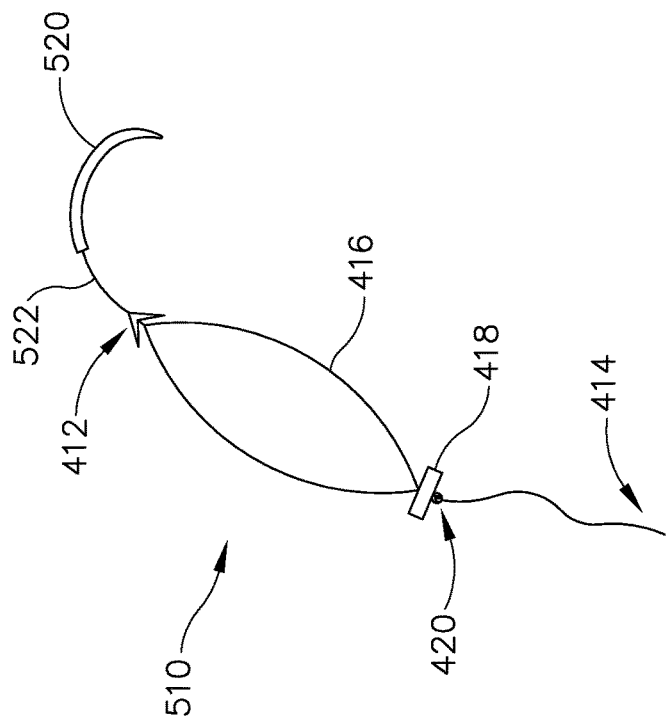
FIG. 16 depicts a partially schematic view of another exemplary alternative suture.
Figure 15:
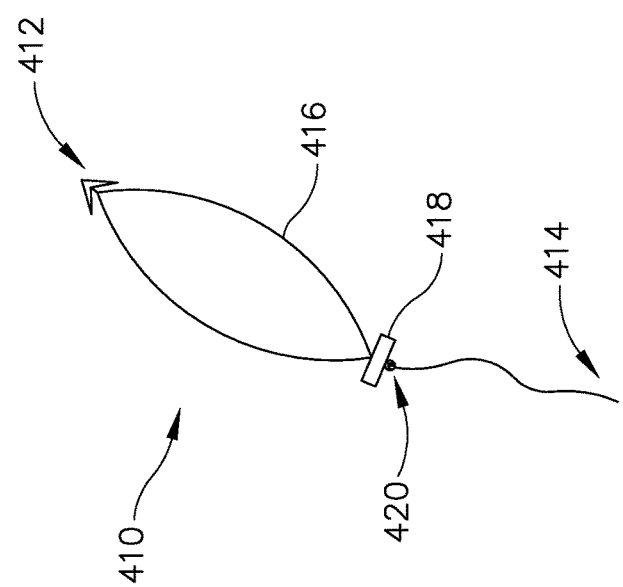
FIG. 15 depicts a partially schematic view of an exemplary alternative suture.

FIG. 16 shows another exemplary alternative suture (510) which is configured to secure one or more of turbinates (110, 130, 140) to the nasal septum (145). In the example shown, suture (510) is substantially similar to suture (410), and therefore like reference numerals are used to identify like components. However, suture (510) is different than suture (410) in that suture (510) includes a needle (520) coupled to barb (412) via an additional length (522) of suture or other material. In the present example, needle (520) is a curved needle including a sharp end, but in other examples needle (520) may include different configurations. Other suitable configurations of needle (520) and suture (510) will be apparent to persons skilled in the art in view of the teachings herein.

Figure 17B:
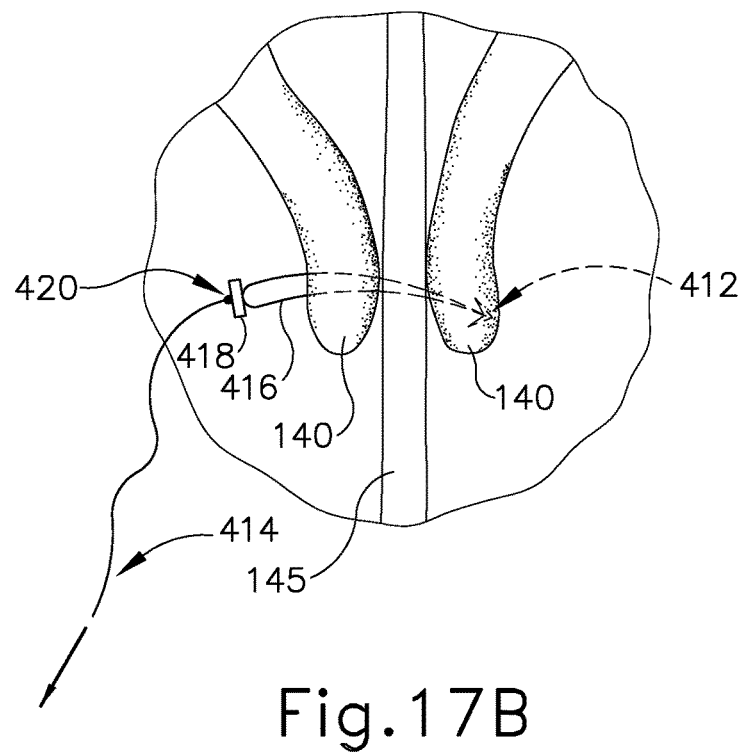
FIG. 17B depicts an anterior coronal cross-sectional view of the portion of a head of the patient of FIG. 17A, showing the suture of FIG. 15 after being inserted into the nasal cavity of the patient and having been directed into a middle turbinate and nasal septum, showing a slip knot feature of the suture in a loose state.
Figure 17C:
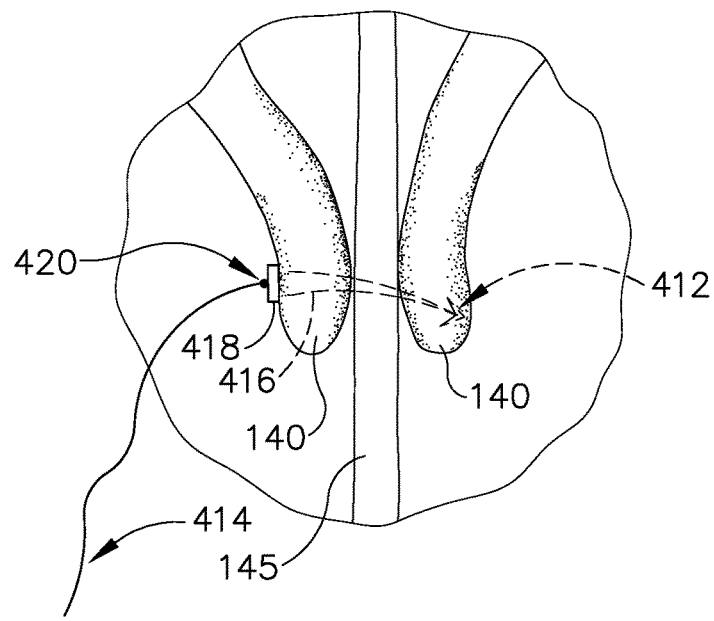
FIG. 17C depicts an anterior coronal cross-sectional view of the portion of a head of the patient of FIG. 17A, showing the suture of FIG. 15 after being inserted into the nasal cavity of the patient and having been directed into a middle turbinate and nasal septum, showing a slip knot of the suture in a tightened state.

Referring to FIGS. 17A-17C, an exemplary alternative method for securing a turbinate to nasal septum (145) includes utilizing suture (410). As shown in FIG. 17A, a user directs suture (410) into a nostril (80) of a patient such that a barb (412) is positioned adjacent to middle turbinate (140), oriented toward the lateral side of middle turbinate (140). The user may direct suture (410) into the nasal cavity using an instrument like instrument (200), or another suitable instrument. Suitable manners of introducing suture (410) into the nasal cavity will be apparent to persons skilled in the art in view of the teachings herein. Once barb (412) is adjacent to turbinate (140), the user may direct barb (412) medially toward turbinate (140) and septum (145). As shown, barb (412) is directed at a downward (e.g., inferior-medial) angle relative to turbinates (140) and septum (145) such that barb (412) penetrates both middle turbinates (140) and septum (145). However, the angle of penetration of anatomical structures may be different than that shown and may change on the configuration of the instrument or method used. As shown in FIG. 17B, loop portion (416) extends through both middle turbinates (140) and septum (145), with barb (412) anchored in the opposing turbinate (140).

Once barb (412) is properly anchored, the user pulls on free end (414) of suture (410) to draw anchor (418) toward turbinate (140) and septum (145) via slip knot (420). As shown in FIG. 17C, the user pulls free end (414) of suture (410) to cause slip knot (420) to urge anchor (418) toward middle turbinate (140) until anchor (418) abuts or bottoms out against middle turbinate (140). The user may continue pulling free end (414) until the turbinates (140) are secured a sufficient amount. In particular, the user pulls free end (414) until both turbinates (140) are medialized against the septum. Finally, the user may sever a portion of free end (414). Barb (412), anchor (418), and slip knot (420) will cooperate to maintain tension in the remaining portion of suture (410), thereby holding both turbinates (140) in a medialized state.

It will be understood that the steps shown in FIGS. 17A-17C may be performed utilizing suture (510). In such a method, a user inserts suture (510) into nostril (180) of the patient until needle (520) is adjacent to one of the middle turbinates (140). The user directs needle (520) through turbinates (140) and septum (145) until anchor reaches the position shown in FIG. 17B-17C, for example. As such, suture (510) is configured such that when barb (412) is suitably positioned, needle (520) is accessible by the user in order to sever or otherwise decouple needle (520) from suture (510) by cutting additional length (522) from barb (412). Once barb (412) is properly anchored, the user pulls on free end (414) of suture (410) to draw anchor (420) towards turbinate (140) and septum (145) via slip knot (420). As shown in the present example, the user pulls free end (414) of suture (410) to cause slip knot to urge anchor (418) towards middle turbinate (140) until anchor (418) abuts or bottoms out against middle turbinate (140). The user may continue pulling free end (414) until the turbinates (140) are secured a sufficient amount such that both turbinates (140) are medialized against the septum. Finally, the user may sever a portion of free end (414), as well as needle (520). Barb (412), anchor (418), and slip knot (420) will cooperate to maintain tension in the remaining portion of suture (510), thereby holding both turbinates (140) in a medialized state.

Suture (210, 310, 410, 510) may comprise any suitable suture material(s) and may be degradable suture or non-degradable. "Degradable (also referred to as "biodegradable" or "bioabsorbable") suture" refers to a suture which, after introduction into a tissue is broken down and absorbed by the body. The degradation process may be at least partially mediated by, or performed in, a biological system. "Degradation" refers to a chain scission process by which a polymer chain is cleaved into oligomers and monomers. Chain scission may occur through various mechanisms, including, for example, by chemical reaction (e.g., hydrolysis, oxidation/reduction, enzymatic mechanisms or a combination of these) or by a thermal or photolytic process. Polymer degradation may be characterized, for example, using gel permeation chromatography (GPC), which monitors the polymer molecular mass changes during erosion and breakdown. Degradable suture material may include polymers such as polyglycolic acid, copolymers of glycolide and lactide, copolymers of trimethylene carbonate and glycolide with diethylene glycol (e.g., MAXON™, Tyco Healthcare Group), terpolymer composed of glycolide, trimethylene carbonate, and dioxanone (e.g., BIOSYN™ [glycolide (60%), trimethylene carbonate (26%), and dioxanone (14%)], Tyco Healthcare Group), copolymers of glycolide, caprolactone, trimethylene carbonate, and lactide (e.g., CAPROSYN™, Tyco Healthcare Group). These sutures can be in either a braided multifilament form or a monofilament form. The polymers used can be linear polymers, branched polymers or multi-axial polymers. Examples of multi-axial polymers used in sutures are described in U.S. Pat. Pub. No. 2002/0161168, entitled "AMORPHOUS POLYMERIC POLYAXIAL INITIATORS AND COMPLIANT CRYSTALLINE COPOLYMERS THEREFROM," published Oct. 31, 2002 (now abandoned), the disclosure of which is incorporated by reference herein; U.S. Pat. No. 7,026,437, entitled "AMORPHOUS POLYMERIC POLYAXIAL INITIATORS AND COMPLIANT CRYSTALLINE COPOLYMERS THEREFROM," issued on Apr. 11, 2006, the disclosure of which is incorporated by reference herein; and U.S. Pat. No. 7,070,858, entitled "AMORPHOUS POLYMERIC POLYAXIAL INITIATORS AND COMPLIANT CRYSTALLINE COPOLYMERS THEREFROM," and issued on Jul. 4, 2006, the disclosure of which is incorporated by reference herein. Sutures made from degradable suture material lose tensile strength as the material degrades.

"Non-degradable (also referred to as "non-absorbable") suture" refers to a suture comprising material that is not degraded by chain scission such as chemical reaction processes (e.g., hydrolysis, oxidation/reduction, enzymatic mechanisms or a combination of these) or by a thermal or photolytic process. Non-degradable suture material includes polyamide (also known as nylon, such as nylon 6 and nylon 6.6), polyester (e.g., polyethylene terephthlate), polytetrafluoroethylene (e.g., expanded polytetrafluoroethylene), polyether-ester such as polybutester (block copolymer of butylene terephthalate and polytetra methylene ether glycol), polyurethane, metal alloys, metal (e.g., stainless steel wire), polypropylene, polyethelene, silk, and cotton. Sutures made of non-degradable suture material are suitable for applications in which the suture is meant to remain permanently or is meant to be physically removed from the body.

Moreover, in some examples, in addition or in the alternative to the materials discussed above, suture (210, 310, 410, 510) may comprise anti-inflammatory materials or medications including, but not limited to, corticosteroids, in order to reduce post-surgical inflammation. In such examples, suture (210, 310, 410, 510) may be coated with such anti-inflammatory materials and/or may be otherwise configured to elute the anti-inflammatory materials after introduction of the suture (210, 310, 410, 510) in tissue. Such materials may reduce post-surgical inflammation.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of securing a turbinate to a nasal septum, the method comprising: (a) positioning an instrument in a nostril; (b) piercing the turbinate and nasal septum; (c) using the instrument to urge a barbed suture through the pierced turbinate and nasal septum; and (d) medializing the turbinate against the nasal septum by urging the turbinate against the septum; wherein the barbed suture holds the turbinate in a medialized state.

Example 2

The method of Example 1, wherein the barbed suture comprises: (i) at least one barb, and (ii) an anchor, wherein the at least one barb is configured to prevent movement of the barbed suture in a lateral direction relative to the septum, wherein the anchor is operable to restrict movement of the barbed suture in a medial direction relative to the septum.

Example 3

The method of Example 2, wherein the act of medializing the turbinate against the nasal septum comprises driving the anchor medially against the turbinate in response to the act of pulling the barbed suture through the pierced turbinate.

Example 4

The method of any one or more of Examples 1 through 3, wherein the act of piercing the turbinate and nasal septum comprises pushing a needle through the turbinate and nasal septum.

Example 5

The method of Example 4, wherein the act of using the instrument to urge the barbed suture through the pierced turbinate and nasal septum comprises pulling the needle.

Example 6

The method of any one or more of Examples 1 through 5, wherein the barbed suture comprises: (i) an anchor, and (ii) a slip knot operably coupled to the anchor, wherein the anchor is responsive to the slip knot.

Example 7

The method of Example 6, wherein the suture comprises a proximal end, wherein the act of medializing the turbinate against the nasal septum comprises pulling the proximal end of the suture while the anchor is positioned against the turbinate.

Example 8

The method of Example 7, wherein the barbed suture further comprises a loop of suture positioned distally of the anchor, wherein the loop has a length that decreases in response to the act of pulling the proximal end of the suture while the anchor is positioned against the turbinate.

Example 9

The method of Example 8, wherein the barbed suture further comprises a barb positioned at a distal end of the loop of barbed suture.

Example 10

The method of any one or more of Examples 1 through 9, wherein the suture is degradable, the method further comprising leaving the barbed suture in the turbinate and septum for a sufficient duration to allow the barbed suture to at least partially degrade.

Example 11

The method of any one or more of Examples 1 through 9, wherein the barbed suture is non-degradable.

Example 12

The method of Example 11, wherein the method further comprises removing the barbed suture from the turbinate and septum.

Example 13

The method of any one or more of Examples 1 through 12, wherein the barbed suture comprises a therapeutic material, the method further comprising allowing the barbed suture to remain in the turbinate and septum for a sufficient time to enable the therapeutic substance to act on one or both of the turbinate or septum.

Example 14

The method of any one or more of Examples 1 through 13, wherein the instrument comprises a shaft defining a lumen, wherein the barbed suture is secured to a needle, wherein the needle is disposed in the lumen during the act of positioning the instrument in the nostril, wherein the barbed suture is stored in the lumen, wherein the barbed suture is pulled from the lumen as the barbed suture is urged through the pierced turbinate and nasal septum.

Example 15

The method of any one or more of Examples 1 through 14, wherein the instrument comprises a shaft, wherein the barbed suture is secured to a needle, the method further comprising pivoting the needle away from a longitudinal axis of the shaft, wherein the act of pivoting the needle is performed between the act of positioning the instrument and the act of piercing the turbinate and nasal septum.

Example 16

A method of securing a turbinate to a nasal septum, the method comprising: (a) inserting a suture into a nasal cavity of a patient, wherein the suture comprises an anchor at a proximal end and at least one barb; and (b) directing the suture through the turbinate and the nasal septum until the anchor engages the turbinate, thereby urging the turbinate medially into apposition with the septum; wherein the anchor and the at least one barb cooperate to maintain tension in the suture to thereby hold the turbinate in medialized apposition with the septum.

Example 17

The method of Example 16, wherein the step of inserting a suture into a nasal cavity of a patient comprises inserting an instrument into a nasal cavity of a patient, wherein the instrument comprises a needle pivotably and removably coupled to a shaft of the instrument, wherein the suture is coupled to the needle.

Example 18

The method of Example 17, wherein the step of directing the suture through the turbinate and the nasal septum further comprises: (i) pivoting the needle relative to the shaft of the instrument, from a stored position to a ready position, (ii) directing a tip of the needle through the turbinate and the nasal septum, (iii) translating the needle relative to the shaft and further through the turbinate and the nasal septum, and (iv) further translating the needle until the needle passes fully through the nasal septum and a sufficient length of suture is passed through the turbinate and the nasal septum.

Example 19

The method of any one or more of Examples 16 through 18, wherein engaging the turbinate with the anchor further comprises utilizing a slip knot mechanism of the suture to draw the anchor toward the turbinate.

Example 20

A method of securing two turbinates to a nasal septum, the method comprising: (a) directing a barbed suture through a first turbinate and the nasal septum, wherein the first turbinate is associated with a first side of the nasal septum; (b) further directing the suture such that a portion of the suture passes through a second side the nasal septum, wherein the second side is opposite to the first side; (c) further directing the suture through a second turbinate, wherein the second turbinate is associated with the second side of the nasal septum; and (d) urging the first and second turbinates medially into apposition with the nasal septum; wherein the barbed suture maintains tension to thereby hold the first and second turbinates in medialized apposition with the septum.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of securing a turbinate to a nasal septum, the method comprising:
   (a) positioning an instrument in a nostril;
   (b) piercing the turbinate and nasal septum;
   (c) using the instrument to urge a barbed suture through the pierced turbinate and nasal septum such that at least one barb of the barbed suture passes from a first side of the nasal septum to a second side of the nasal septum; and
   (d) medializing the turbinate against the nasal septum by urging the turbinate against the nasal septum;
   wherein the at least one barb of the barbed suture engages the second side of the nasal septum and thereby holds the turbinate in a medialized state against the nasal septum.

2. The method of claim 1, wherein the barbed suture comprises:
   (i) at least one barb, and
   (ii) an anchor, wherein the at least one barb is configured to prevent movement of the barbed suture in a lateral direction relative to the septum, wherein the anchor is operable to restrict movement of the barbed suture in a medial direction relative to the septum.

3. The method of claim 2, wherein the act of medializing the turbinate against the nasal septum comprises driving the anchor medially against the turbinate in response to the act of pulling the barbed suture through the pierced turbinate.

4. The method of claim 1, wherein the act of piercing the turbinate and nasal septum comprises pushing a needle through the turbinate and nasal septum.

5. The method of claim 4, wherein the act of using the instrument to urge the barbed suture through the pierced turbinate and nasal septum comprises pulling the needle.

6. The method of claim 1, wherein the barbed suture comprises:
   (i) an anchor, and
   (ii) a slip knot operably coupled to the anchor, wherein the anchor is responsive to the slip knot.

7. The method of claim 6, wherein the suture comprises a proximal end, wherein the act of medializing the turbinate against the nasal septum comprises pulling the proximal end of the suture while the anchor is positioned against the turbinate.

8. The method of claim 7, wherein the barbed suture further comprises a loop of suture positioned distally of the anchor, wherein the loop has a length that decreases in response to the act of pulling the proximal end of the suture while the anchor is positioned against the turbinate.

9. The method of claim 8, wherein the barbed suture further comprises a barb positioned at a distal end of the loop of barbed suture.

10. The method of claim 1, wherein the suture is degradable, the method further comprising leaving the barbed suture in the turbinate and septum for a sufficient duration to allow the barbed suture to at least partially degrade.

11. The method of claim 1, wherein the barbed suture is non-degradable.

12. The method of claim 11, wherein the method further comprises removing the barbed suture from the turbinate and septum.

13. The method of claim 1, wherein the barbed suture comprises a therapeutic material, the method further comprising allowing the barbed suture to remain in the turbinate and septum for a sufficient time to enable the therapeutic substance to act on one or both of the turbinate or septum.

14. The method of claim 1, wherein the instrument comprises a shaft defining a lumen, wherein the barbed suture is secured to a needle, wherein the needle is disposed in the lumen during the act of positioning the instrument in the nostril, wherein the barbed suture is stored in the lumen, wherein the barbed suture is pulled from the lumen as the barbed suture is urged through the pierced turbinate and nasal septum.

15. The method of claim 1, wherein the instrument comprises a shaft, wherein the barbed suture is secured to a needle, the method further comprising pivoting the needle away from a longitudinal axis of the shaft, wherein the act of pivoting the needle is performed between the act of positioning the instrument and the act of piercing the turbinate and nasal septum.

16. A method of securing a turbinate to a nasal septum, the method comprising:
   (a) positioning an instrument in a nostril;
   (b) piercing the turbinate and nasal septum with a needle;
   (c) urging the needle and a barbed suture out of the instrument and through the pierced turbinate and nasal septum;
   (d) engaging a first side of the nasal septum with at least one barb of the barbed suture; and
   (e) medializing the turbinate against a second side of the nasal septum by urging the turbinate against the second side nasal septum;
   wherein the at least one barb engaging the first side of the nasal septum maintains tension against the nasal septum to thereby hold the turbinate in a medialized state against the second side of the nasal septum.

17. The method of claim 16, further comprising positioning a second instrument in an opposite nostril.

18. The method of claim 17, further comprising grasping the needle with the second instrument.

19. The method of claim 18, further comprising urging the needle out of the opposite nostril to generate tension along the barbed suture and thereby medialize the turbinate against the nasal septum.

20. A method of securing a turbinate to a nasal septum, the method comprising:
   (a) positioning an instrument in a nostril;
   (b) piercing the turbinate and nasal septum;
   (c) using the instrument to pass at least one barb of a barbed suture through the pierced turbinate and nasal septum;
   (d) medializing the turbinate against the nasal septum by urging the turbinate against the nasal septum, wherein the at least one barb of the barbed suture engages the nasal septum and thereby holds the medialized turbinate against the nasal septum; and
   (e) severing an excess end portion of the barbed suture.

* * * * *